(12) United States Patent
Kasai et al.

(10) Patent No.: US 8,257,066 B2
(45) Date of Patent: Sep. 4, 2012

(54) TUBING MISLOAD DETECTION MECHANISM FOR AN INFUSION PUMP

(75) Inventors: Takashi Kasai, Tokyo (JP); Kenji Honda, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 464 days.

(21) Appl. No.: 12/429,391

(22) Filed: Apr. 24, 2009

(65) Prior Publication Data

US 2009/0275897 A1 Nov. 5, 2009

Related U.S. Application Data

(63) Continuation-in-part of application No. 12/112,126, filed on Apr. 30, 2008.

(51) Int. Cl.
F04B 43/08 (2006.01)
(52) U.S. Cl. .................................................. 417/474
(58) Field of Classification Search .................. 417/474
See application file for complete search history.

(56) References Cited

U.S. PATENT DOCUMENTS

| | | | |
|---|---|---|---|
| 6,629,955 B2* | 10/2003 | Morris et al. | 604/153 |
| 6,731,216 B2* | 5/2004 | Ho et al. | 340/608 |

FOREIGN PATENT DOCUMENTS

| | | | |
|---|---|---|---|
| JP | H05-15589 A | 1/1993 | |
| JP | H05-277183 A | 10/1993 | |
| JP | 2002-58738 A | 2/2002 | |

OTHER PUBLICATIONS

International Search Report dated Jul. 14, 2009; International Application No. PCT/JP2009/001950; with English translation.
The Written Opinion from International Searching Authority/ Japanese Patent Office dated Jun. 25, 2009; International Application No. PCT/JP2009/001950.

* cited by examiner

*Primary Examiner* — Charles Freay
(74) *Attorney, Agent, or Firm* — Studebaker & Brackett PC; Donald R. Studebaker (57) ABSTRACT

An infusion tube misloading detection mechanism for an infusion pump is provided at a low cost with a safety feature of detecting misloading of infusion tube. When a door unit is to be closed with respect to a pump body in a misloaded state of an infusion tube, a misload detection inner door is pressed by the misloaded infusion tube. Accordingly, an interlock part is prevented from being closed with the pump body. Therefore, the misloaded state can be easily identified.

3 Claims, 10 Drawing Sheets

FIG.10

TUBING MISLOAD DETECTION MECHANISM FOR AN INFUSION PUMP

TECHNICAL FIELD

The present invention relates to a system for preventing misload of an infusion tube in an infusion pump having a door which is used for a medical intravenous apparatus or the like.

BACKGROUND ART

Conventionally, a peristaltic infusion pump is mainly used as a medical infusion pump for feeding a medicinal solution or the like in an infusion tube, in which a door is openably and closably provided to an infusion pump body having a pump mechanism.

The peristaltic infusion pump has a structure for performing feed, in which a plurality of fingers provided to a pump body perform reciprocating motion with individual phases to be in a peristaltic movement as a whole, so that infusion tubes disposed between the fingers and a receiving plate provided to the door are sequentially pressed toward a downstream so as to perform the feed. An example of the peristaltic infusion pump is disclosed in Patent Document 1.

In such an infusion pump, if the infusion tube is not fitted at a correct position, when a door provided to the infusion pump is closed so as to perform infusion, an amount of a fed solution is greatly reduced, or any amount of the solution is not fed. Therefore, an infusion pump having a function of detecting a misloaded state of the infusion tube to prevent the misload of the infusion tube is desired.

As an example of an infusion pump having a function of preventing misload of the infusion tube, a technique of detecting the misload of the tube by using a position detection sensor such as a pressure sensitive sensor to control an alarm about abnormal fitting is disclosed in Patent Document 2.

According to the function of preventing misload of the infusion tube in the infusion pump disclosed in Patent Document 2, the misfit state of the infusion tube is correctly detected, and the alarm is issued based on the detection, so that the misfit state can be speedily released for a proper and prompt response. Therefore, the infusion pump has a good safety as a medical instrument.

[Patent Document 1] Japanese Patent Application Publication No. 5-277183
[Patent Document 2] Japanese Patent Application Publication No. 5-15589

DISCLOSURE OF THE INVENTION

Problems to be Solved

However, according to a conventional method of detecting misload of an infusion tube by using a position detection sensor, the sensor may be expensive, an output of the sensor needs to be adjusted, or software for electrical control needs to be developed. Therefore, the infusion pump may become expensive.

In order to implement an inexpensive infusion pump maintaining safety, it is preferable to provide a means for detecting misload of an infusion tube.

Means for Solving the Problems

In order to solve the problems, the present invention provides a tubing misload detection mechanism for an infusion pump comprising a door, an inner door, and an interlocking part.

The door is supported with a shaft by a pump body of the infusion pump in an openable/closable state; the inner door is supported with a shaft by the door; and when the infusion tube fitted in the pump body presses the inner door, the inner door is moved due to the pressing of the infusion tube.

In the tubing misload detection mechanism for an infusion pump, the interlocking part operates in interlock with the inner door, so that the door is prevented from being stably held in the pump body.

In the tubing misload detection mechanism for an infusion pump, the interlocking part is disposed to a handle provided to the door in the tubing misload detection mechanism for an infusion pump.

The door can be locked with the pump body by inserting a claw portion provided to the interlocking part into a through-hole provided to the pump body.

In the tubing misload detection mechanism for an infusion pump, when the interlocking part operates in interlock with the movement of the inner door, the claw portion of the interlocking part is moved, so that the door is prevented from being stably held in the pump body.

In the tubing misload detection mechanism for an infusion pump, the interlocking part is disposed inside the door in the tubing misload detection mechanism for an infusion pump.

The interlocking part has a prismatic-column-shaped or circular-column-shaped protrusion portion, the protrusion portion is disposed inside the door, and the interlocking part operates in interlock with the movement of the inner door.

In the tubing misload detection mechanism for an infusion pump, the protrusion portion protrudes to an outside of the door and to a position in a pivotable range where the operation of the handle provided to the door is prevented, so that the door is prevented from being stably held in the pump body.

In the tubing misload detection mechanism for an infusion pump, at the time of detection of misleading of the infusion tube in the tube misload detection mechanism of an infusion pump, a thickness of a surface of the inner door which presses the infusion tube is increased as a distance of the position thereof from a door supporting shaft is increased.

Effect of the Invention

According to the invention when the infusion tube is misloaded, a manipulator can visually identify the state that the door is not entirely closed, so that the misloaded state of the infusion tube can be detected.

Since the misloaded state of the infusion tube can be detected by using a mechanical structure without use of an electrical position detection sensor, the misloading of the infusion tube can be detected irrespective of abnormality of sensitivity of a sensor due to a use environment or electrical problems such as disconnection of electrical wire lines.

Since conventional expensive senor or electrical circuits are not needed, a task or facility for adjusting sensitivity of sensor in a production process for the infusion pump is not needed, so that it is possible to implement a tubing misload detection mechanism for an infusion pump at a low cost with a safety maintained.

According to the invention since a force exerted from an inner door can be directly exerted on the interlocking part, it is possible to implement a tubing misload detection mechanism for an infusion pump with a simple structure.

According to the invention in addition to implementation of the misload detection mechanism at a low cost, a protrusion portion which is provided to a position where the operation of the handle is prevented is suitable. Therefore, the invention can be applied to any types of handles including handles having various shapes or handles having no lock mechanism.

BEST MODE FOR CARRYING OUT THE INVENTION

According to the invention the misloaded state of the infusion tube can be detected at a high accuracy irrespective of a position where the infusion tube is misloaded.

BEST MODE FOR CARRYING OUT THE INVENTION

Hereinafter, tubing misload detection mechanisms for an infusion pumps according to preferred embodiments of the present invention will be described with reference to the accompanying drawings. In the embodiments, the same elements are denoted by the same reference numerals.

First Embodiment

In a tube misload detection mechanism according to a first embodiment of the present invention, a door cannot be locked with a pump body in a closed state thereof when an infusion tube is not loaded at a correct position in the pump body, so that a misloaded state of the infusion tube can be detected.

More specifically, when the door is to be closed in a state that the infusion tube is not correctly loaded to a groove of the pump body, the infusion tube presses an inner door provided to the door, so that a force due to the pressing is transferred to a claw-shaped part that enables the door to be locked with the pump body. Therefore, the claw-shaped part is moved to a position where the door cannot be locked to be held in a stable state.

Hereinafter, structures and functions of a tube misload detection mechanism and an infusion pump using the tube misload detection mechanism according to the embodiment will be described in detail.

[Infusion Pump]

Figure 1:
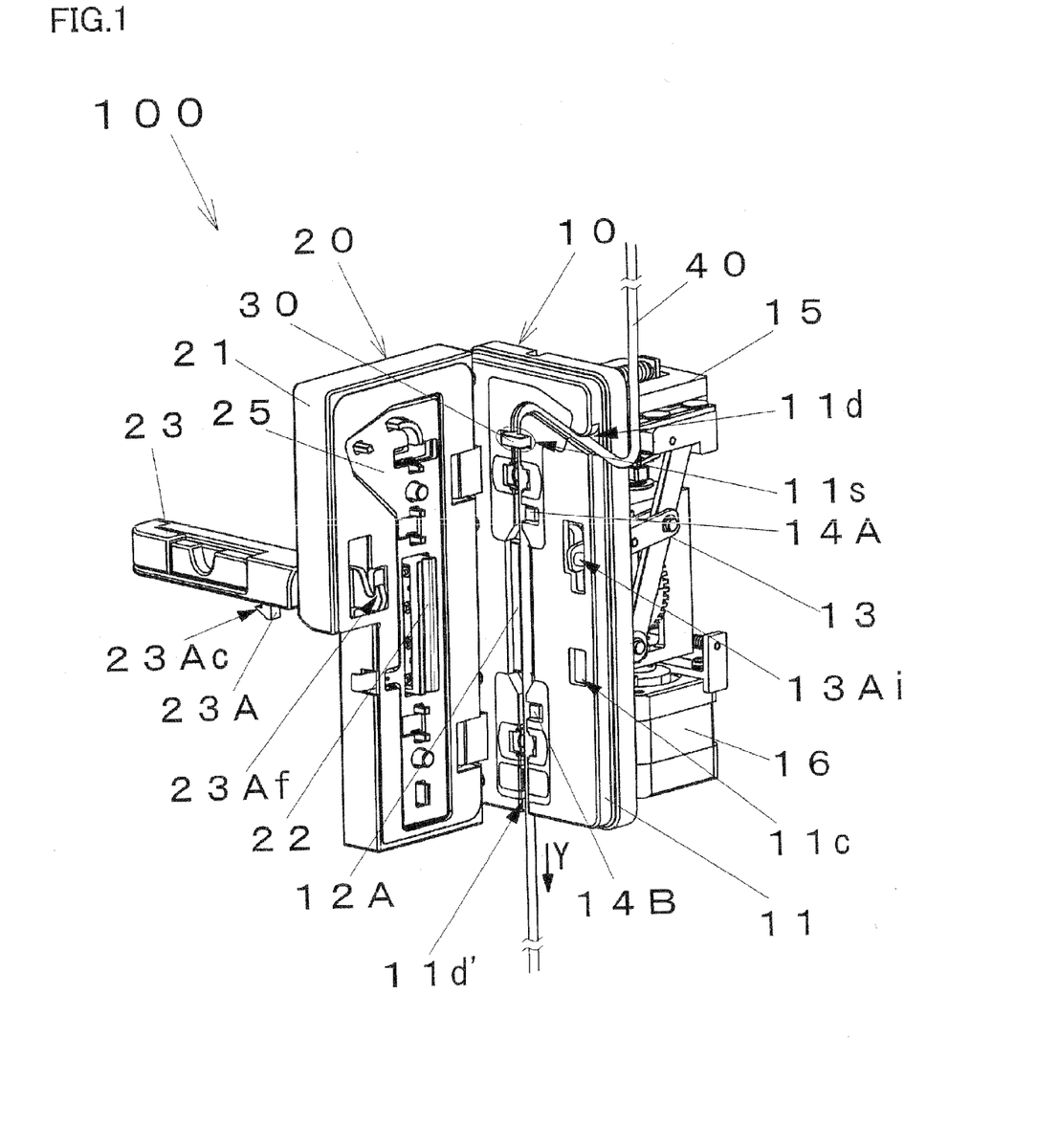
FIG. 1 is a perspective view illustrating an infusion pump having a tube misload detection mechanism according to an embodiment of the present invention.

FIG. 1 is a perspective view illustrating an infusion pump 100 having the tube misload detection mechanism according to the first embodiment of the present invention. The infusion pump 100 is mainly constructed with a pump body 10 and a door unit 20 which is openably and closably provided to the pump body 10. In FIG. 1, the door unit 20 is in an opened state.

The pump body 10 is mainly constructed with a valve mechanism part having a valve 14A and a valve 14B, a slide clamp mechanism part 15, an interlock mechanism part 13, a shuttle mechanism part having a V-grooved driving part 12A, and a motor 16, which are disposed on a base plate 11.

The door unit 20 is mainly constructed with a handle 23 provided to a door part 21, a V-grooved fixing part 22, and a misload detection inner door 25.

The infusion tube 40 is loaded in the pump body 10 in a state that the infusion tube is closed by a slide clamp 30 which is a clamp member for the infusion tube.

As shown in FIG. 1, the infusion tube 40 closed by the slide clamp 30 is loaded at the correct position in a state that a portion of the slide clamp 30 is mounted on a slide clamp mounting portion 11s of the base plate 11 and the other portions are mounted on the groove portion 11d-11d'.

Figure 2:
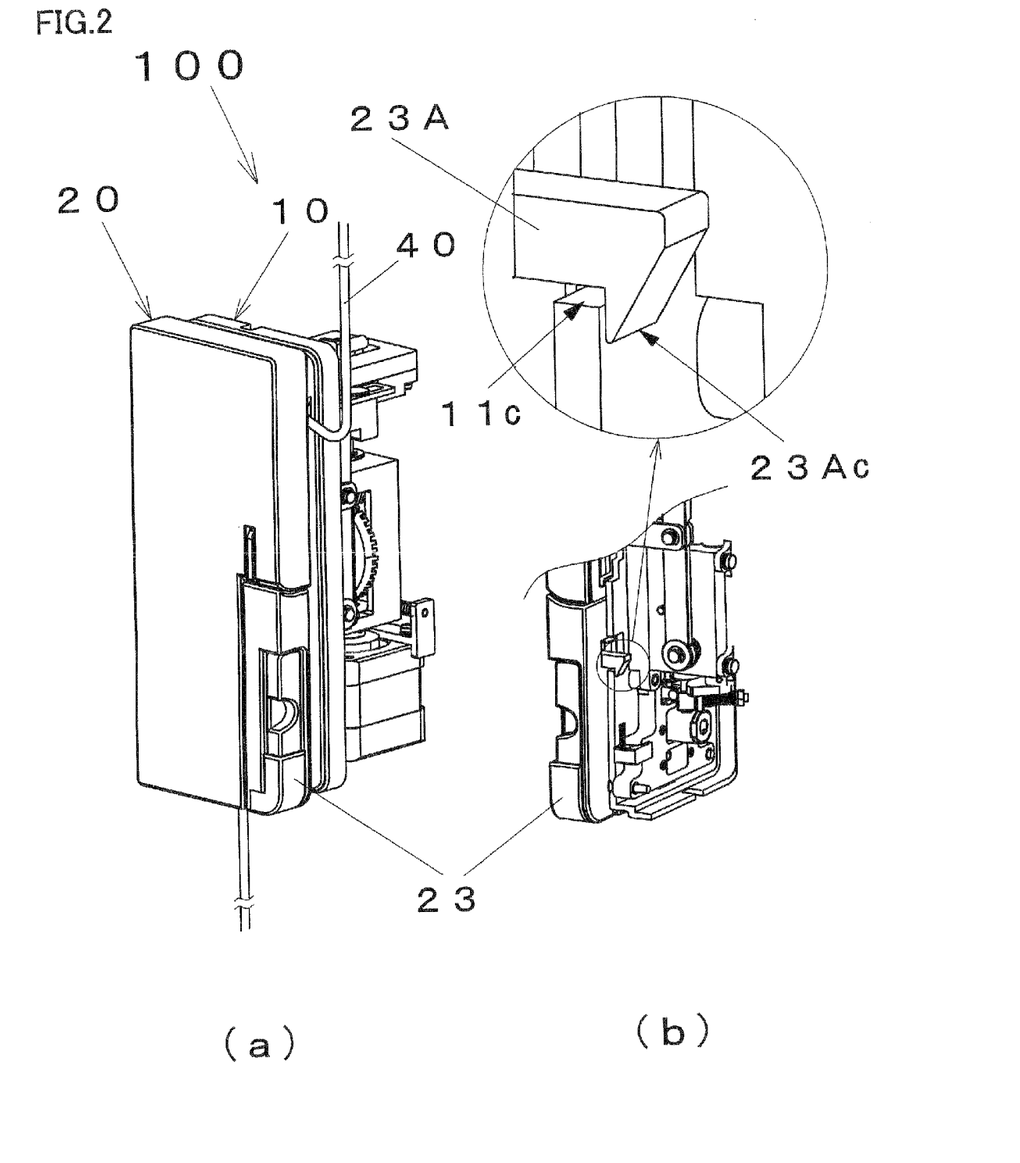
FIG. 2 is a view illustrating a state that the infusion pump according to the embodiment of the present invention is correctly loaded in a pump body.

FIG. 2(a) illustrates a state that the door unit 20 is entirely closed with respect to the pump body 10 after the infusion tube is loaded at the correct position in the pump body.

As shown in FIG. 2(b), in the state that the door unit 20 is entirely closed with respect to the pump body 10, a claw portion 23Ac of a handle lock part 23A provided to the handle 23 is inserted into a rectangular through-hole 11c of the base plate 11 so as to be locked with the pump body 10.

In the state shown in FIG. 2(a) that the infusion tube 40 is loaded at the correct position and the door unit is closed, the infusion pump 100 feeds a solution by allowing the V-grooved driving part 12A to perform reciprocating motion in a direction perpendicular to the feeding direction and in a direction parallel to the V-grooved fixing part 22 opposite thereto so that the V-grooved fixing part 22 may repetitively press the infusion tube.

According to the tube misload detection mechanism of the embodiment, when the infusion tube 40 is not fitted at the correct position in the pump body 10, the door unit 20 cannot be locked with the pump body 10 in the closed state thereof, so that the infusion pump 100 can be prevented from being used in the misloaded state of the infusion tube 40.

[Tube Misload Detection Mechanism]

Figure 3:
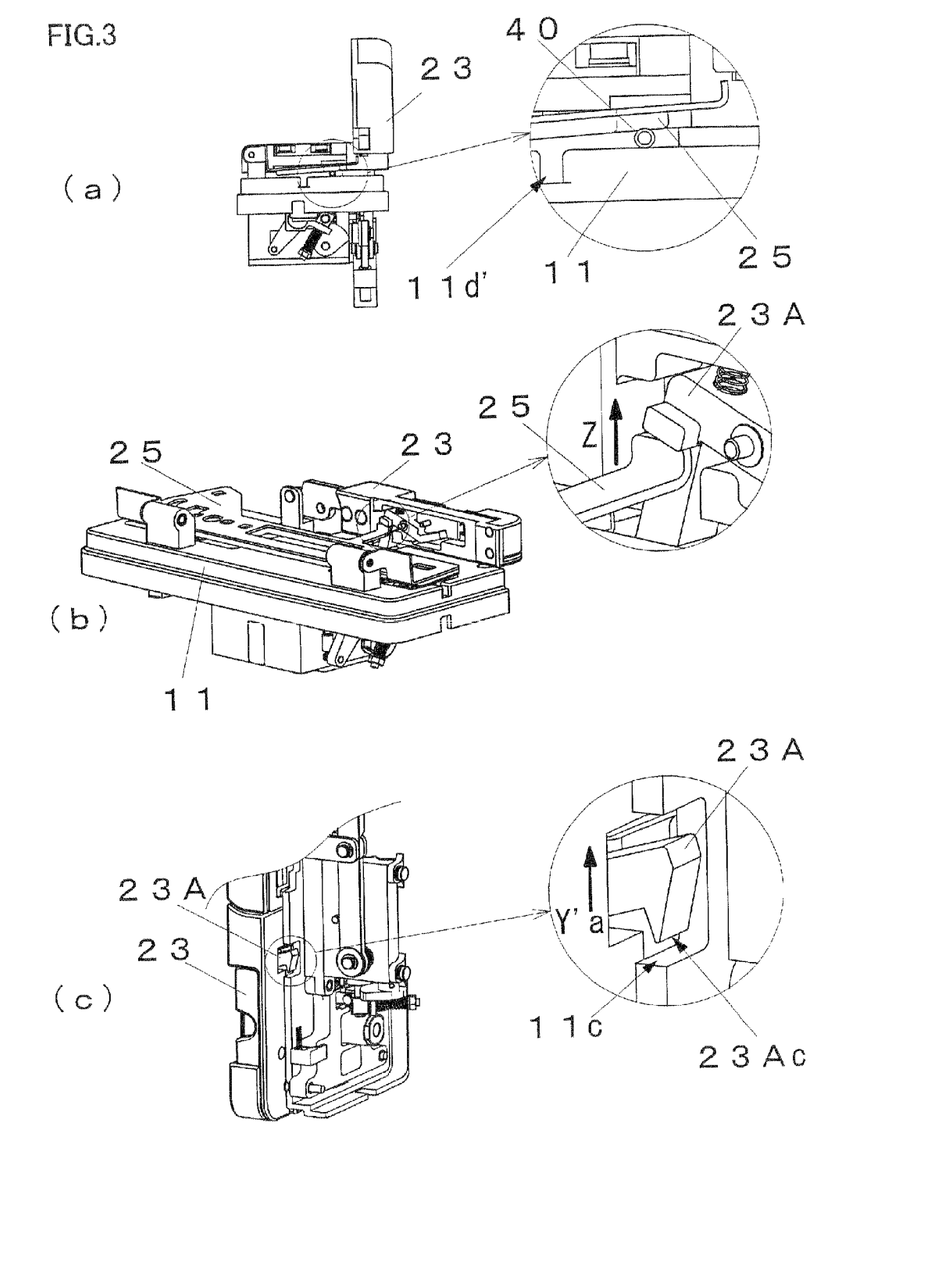
FIG. 3 is a view illustrating a state that the infusion pump according to the embodiment of the present invention is not correctly loaded in the pump body.

FIG. 3(a) is a bottom view of the infusion pump 100 illustrating a state that the infusion tube 40 is misloaded in the infusion pump 100.

When the infusion tube 40 is fitted correctly, the infusion tube passes by the groove portion 11d' of the base plate 11. However, as shown in FIG. 3(a), when the infusion tube is not correctly loaded, the infusion tube 40 is interposed between a portion excluding the groove portion 11d-11d' of the base plate 11 and the misload detection inner door 25.

In this case, the misload detection inner door 25 is pressed by the infusion tube 40, so that a force is exerted to a handle lock part 23A provided to the handle 23 in the Z direction (see FIG. 3(b)).

Accordingly, a position of the claw portion 23Ac of a handle lock part 23A is moved in the Y'a direction, and the claw portion 23Ac is inserted into a rectangular through-hole 11c of the base plate 11, so that the door unit 20 cannot be locked with the pump body 10 (see FIG. 3(c)).

When the door unit 20 is to be closed with respect to the pump body 10 in the state that the door unit 20 is not locked with the pump body 10, a hook portion 23Af of the handle 23 is hooked with a portion 13Ai of the pump body, or the door unit is in a half-opened state. Therefore, a user can identify the misloaded state.

Second Embodiment

In a tube misload detection mechanism according to a second embodiment of the present invention, a protrusion portion for preventing manipulation of a handle in interlock with pressing of an inner door by the infusion tube when the infusion tube is not fitted at a correct position in a pump body is provided, so that a misloaded state of the infusion tube can be detected.

Hereinafter, a latching method of a door in an infusion pump using a structure of the tube misload detection mechanism according to the embodiment and detailed structure and function of the tube misload detection mechanism will be described.

[Infusion Pump]

Figure 4:
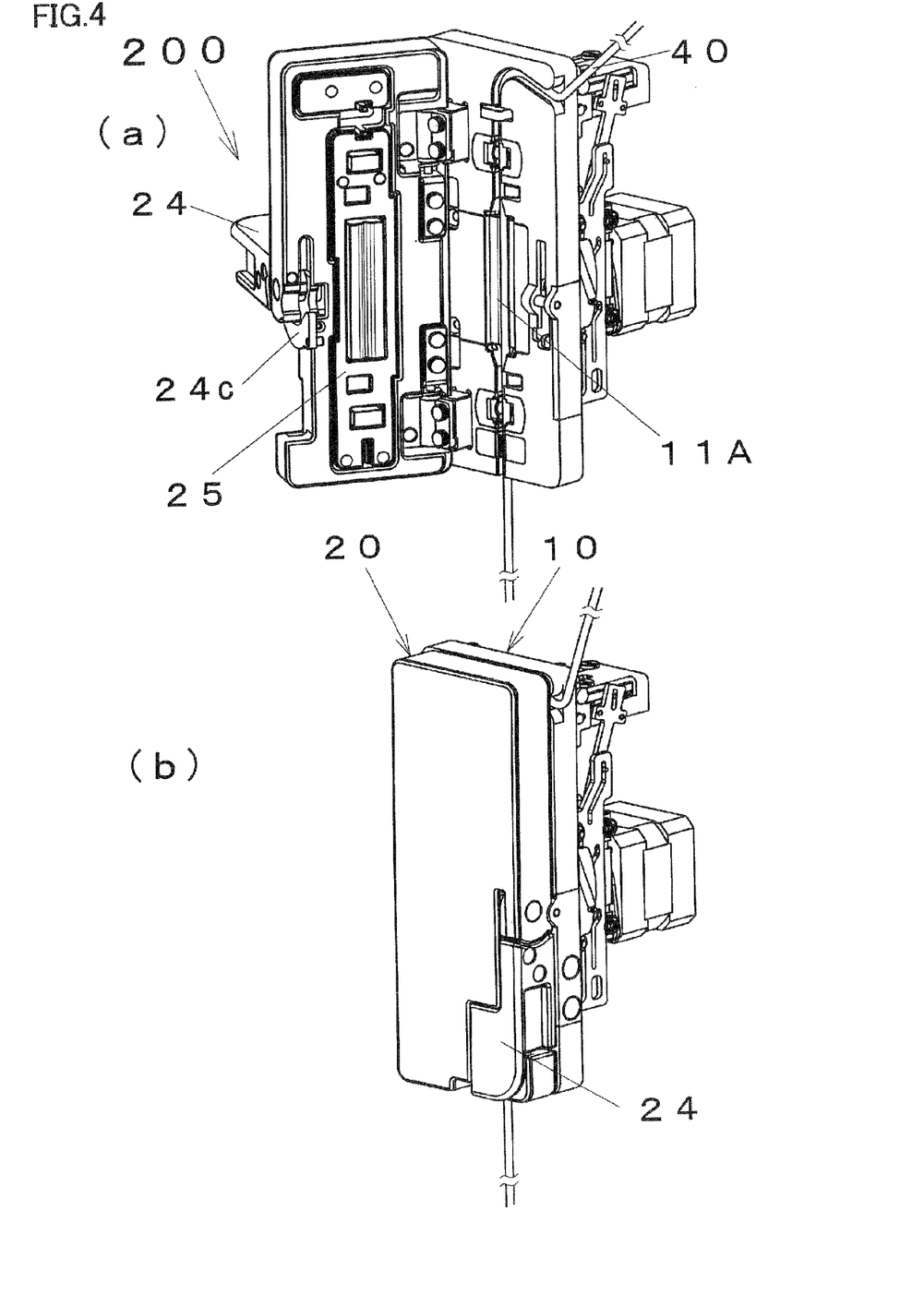
FIG. 4 is a perspective view illustrating an infusion pump having a tube misload detection mechanism according to another embodiment of the present invention.

FIG. 4 is a perspective view illustrating an infusion pump 200 having the tube misload detection mechanism according to the second embodiment of the present invention. The infusion pump 200 is mainly constructed with a pump body 10 and a door unit 20 which is openably and closably provided to the pump body 10. In FIG. 4(a), the door unit 20 is in an opened state.

A basic construction of the infusion pump 200 is the same as that of the infusion pump 100 according to the first embodiment. When the infusion tube is misloaded, the misload detection inner door is pressed so that mechanisms in the door unit 20 are operated. However, in the infusion pump 200, the handle 24 has no handle lock part having a claw portion, and the door unit 20 is locked with the pump body 10 in a different method.

When an infusion tube 40 is fitted at a correct position in the pump body 10, a curved arm portion 24c of the handle 24 is stably in contact with a latch roller 11A provided to a base plate 11 to be inserted into the door unit 20, so that the door unit 20 in the closed state is locked with the pump body 10 to be held in a stable state (see FIG. 4(b)).

[Tube Misload Detection Mechanism]

Figure 5:
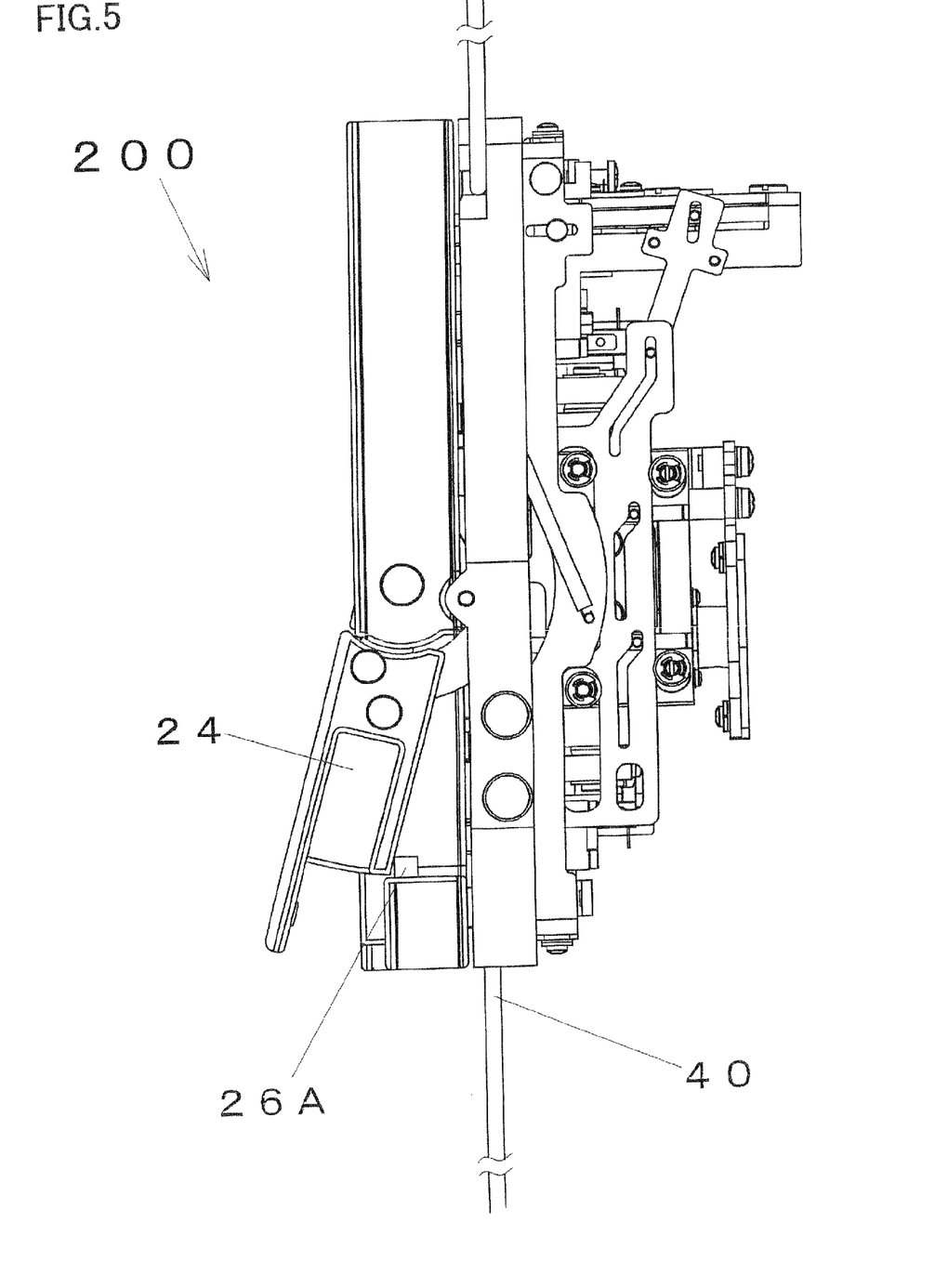
FIG. 5 is a view illustrating a state that the infusion pump according to the embodiment of the present invention is not correctly fitted in the pump body.

FIG. 5 is a view illustrating a misloaded state of the infusion tube 40 in the infusion pump 200. In this case, the misload detection inner door 25 (see FIG. 4(a)) is pressed by the infusion tube 40, and accordingly, a stopper 26A is protruded, so that manipulation of the handle 24 is prevented.

Figure 6:
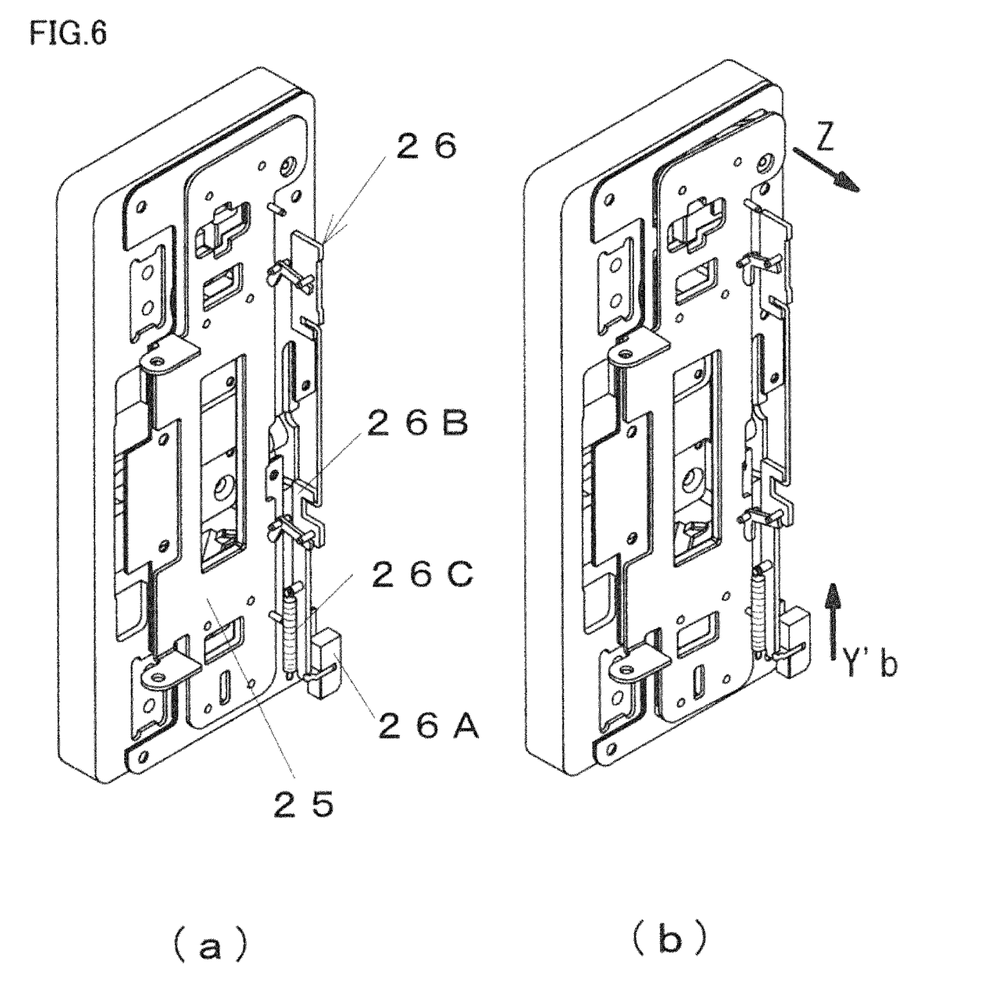
FIG. 6 is a view illustrating a structure of a tube misload detection mechanism according to another embodiment of the present invention.

FIG. 6 is a view illustrating a structure of a stopper mechanism 26 which is cooperatively operated with the mislead detection inner door 25. The stopper mechanism is constructed with a stopper 26A, a stopper holder 26B, and a stopper spring 26C.

FIG. 6(a) is a view illustrating a state of the stopper mechanism 26 when the misload detection inner door 25 is not pressed by the infusion tube 40 due to misloading of the infusion tube 40 at a correct position.

In this case, a stopper spring 26C of which one end is held by the door part presses a stopper holder 26B provided integrally with a prismatic-column-shaped stopper 26A downwards.

FIG. 6(b) is a view illustrating a state of the stopper mechanism 26 when the misload detection inner door 25 is pressed by the infusion tube 40 in the Z direction due to misload of the infusion tube 40.

In this case, as shown in FIG. 5, the misload detection inner door 25 presses the stopper holder 26B provided integrally with the stopper 26A in the Y'b direction so as to protrude the stopper 26A, so that manipulation of the handle 24 can be prevented.

In the embodiment, the prismatic-column-shaped stopper 26A is used. However, a circular-column-shaped stopper can also be used as a suitable protrusion portion for preventing manipulation of the handle 24.

Third Embodiment

In a tube misload detection mechanism according to a third embodiment of the present invention, a position of a part of locking a door is moved in interlock with pressing of an inner door by an infusion tube when the infusion tube is not misloaded at a correct position in a pump body, so that the part of locking the door cannot be locked with the door. Therefore, a misloaded state of the infusion tube can be detected.

Hereinafter, a latching method of a door in an infusion pump using a structure of the tube misload detection mechanism according to the embodiment and structure and function of the tube misload detection mechanism will be described.

Figure 7:
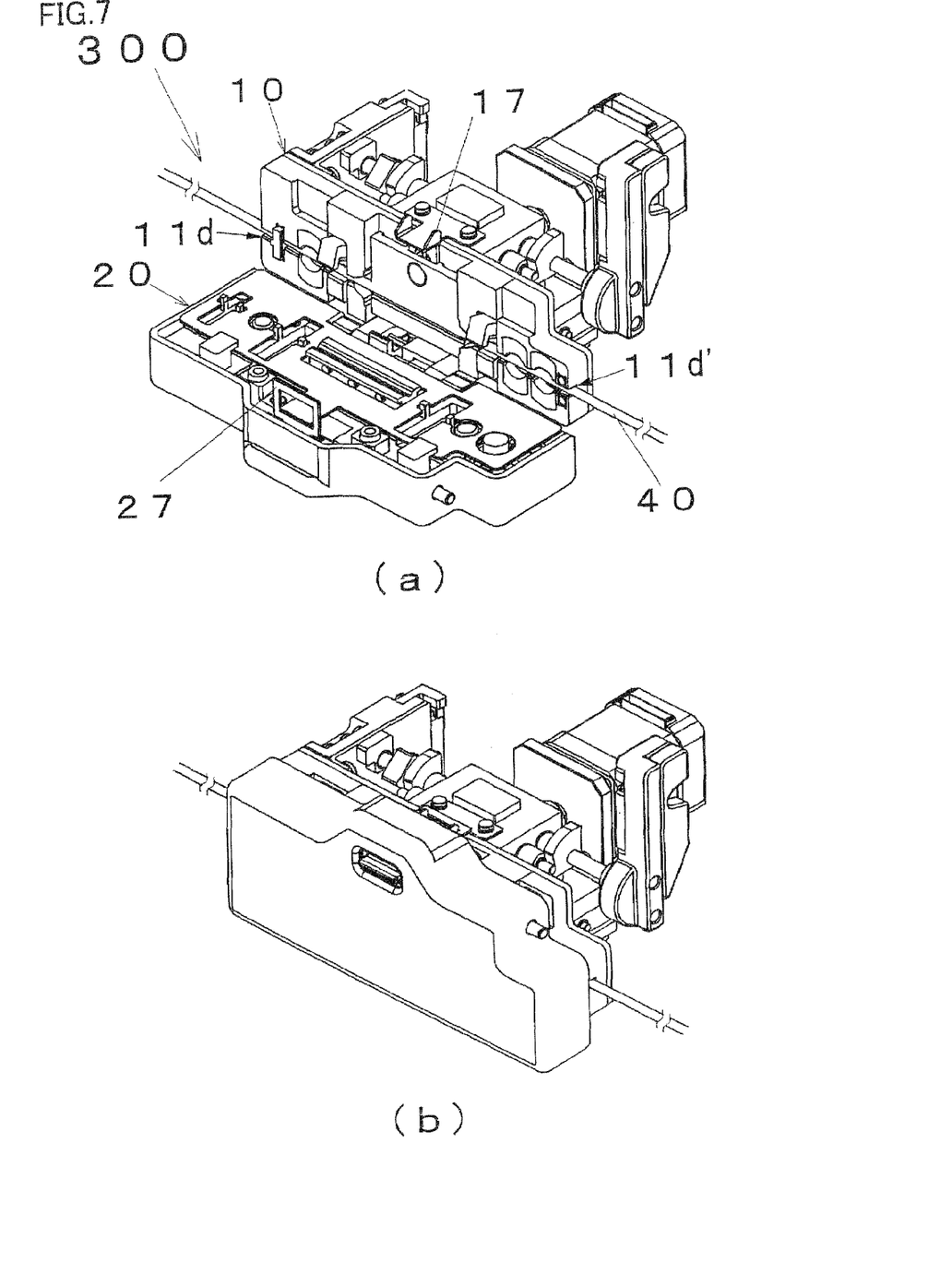
FIG. 7 is a perspective view illustrating an infusion pump having a tube misload detection mechanism according to another embodiment of the present invention.

FIG. 7(a) is a perspective view illustrating an infusion pump 300 having the tube misload detection mechanism according to the third embodiment of the present invention. The infusion pump 300 is mainly constructed with a pump body 10 and a door unit 20 which is openably and closably provided to the pump body 10. In FIG. 7(a), the door unit 20 is in the opened state.

When the infusion tube 40 is fitted at a correct position in the pump body 10, a door lock part 27 is latched with a lock part 17 of the pump body, so that the door unit 20 can be locked with the pump body 10 in the closed state thereof (see FIG. 7(b)).

Figure 8:
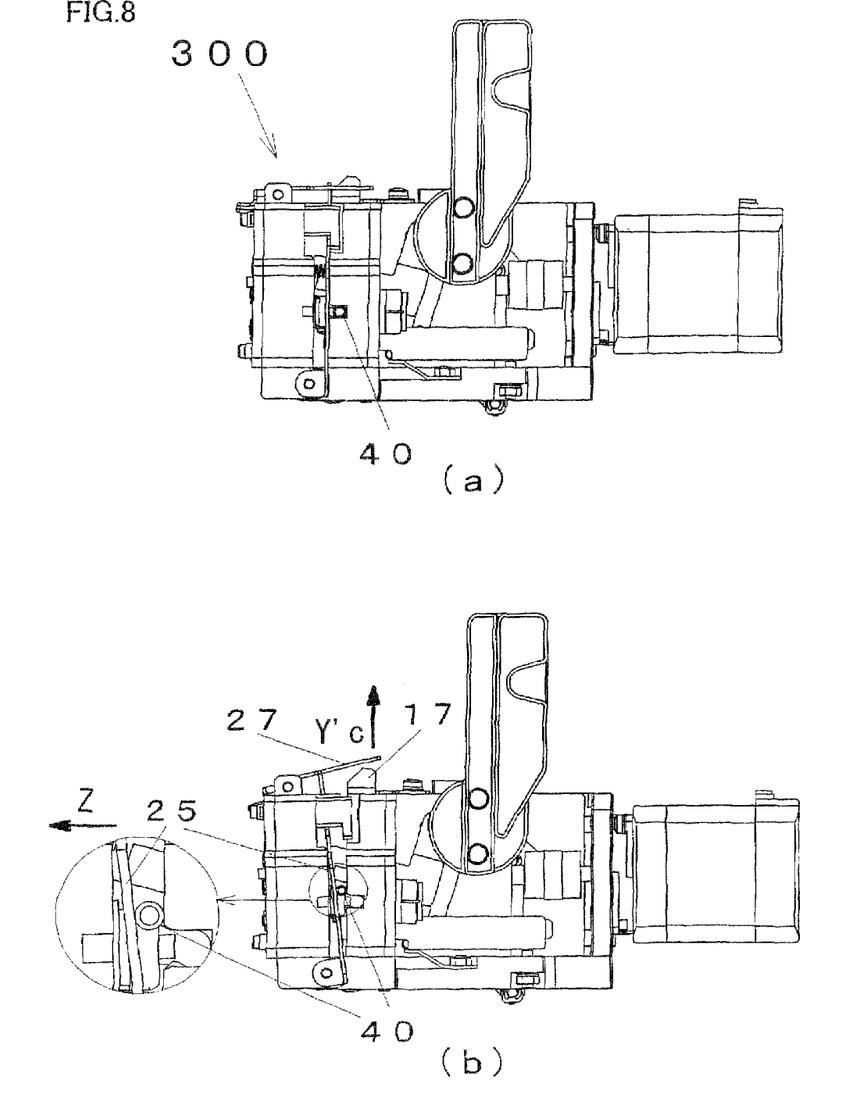
FIG. 8 is a view illustrating a state that the infusion pump according to the embodiment of the present invention is correctly loaded in the pump body and a state that the infusion pump is not correctly loaded.

FIG. 8(a) illustrates a state that the infusion tube 40 is fitted at a correct position in the pump body 10, so that the door unit 20 is closed with respect to the pump body 10. In this case, sine the infusion tube 40 is correctly inserted into the groove portion 11d-11d' of the base plate 11, the infusion tube 40 cannot press the misload detection inner door 25.

FIG. 8(b) illustrates a state that the infusion tube 40 is not correctly inserted into the groove portion 11d-11d' of the base plate 11 but misloaded. In this case, the infusion tube 40 presses the misload detection inner door 25 in the Z direction, and the door lock part 27 is moved in the Y'c direction in interlock with the pressing, so that the door unit 20 cannot be closed with respect to the pump body 10.

Fourth Embodiment

In a tube misload detection mechanism according to a fourth embodiment of the present invention, a thickness of a surface of an inner door which presses a infusion tube is constructed to be increased as a distance of a position thereof from a door supporting shaft is increased. Even in case that the infusion tube is misloaded at a position apart from the door supporting shaft, such misloaded state of the infusion tube can be detected at a high accuracy.

Hereinafter, a shape of an inner door in an infusion pump using a structure of the tube mislead detection mechanism according to the embodiment and functions of the tube mislead detection mechanism will be described in detail.

Figure 9:
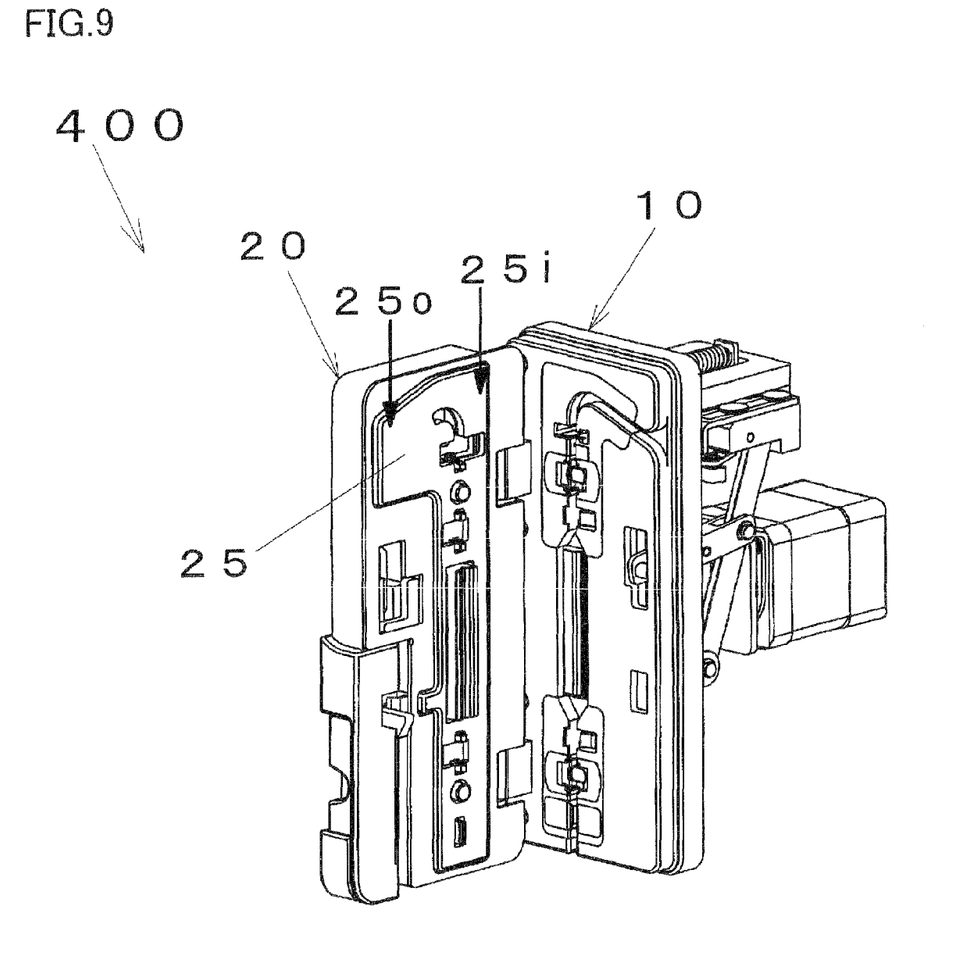
FIG. 9 is a perspective view illustrating an infusion pump having a tube misload detection mechanism according to another embodiment of the present invention.

FIG. 9 is a perspective view illustrating an infusion pump 400 having a tube mislead detection mechanism according to the fourth embodiment of the present invention A basic construction of the tube misload detection mechanism of the infusion pump 400 is the same as that of the infusion pump 100 according to the first embodiment except for a shape of the misload detection inner door 25.

In the misload detection inner door 25 of the door unit 20 in the infusion pump 400, an area of a surface thereof contacting the infusion tube is formed to be as large as possible, within a limit that a problem does not occur in the misload detection mechanism for the infusion tube.

In addition, the surface of the misload detection inner door 25 contacting the infusion tube is formed to have an inclination angle of 1° over a region from a supporting-shaft side portion (a portion near the door supporting shaft) 25i of the door unit 20 to a supporting-shaft opposite-side portion (a portion far from the door supporting shaft) 25o.

Due to the inclined surface having the inclination angle of 1°, a thickness of the surface of the misload detection inner door 25 is increased in a direction from the supporting-shaft side portion 25i toward the supporting-shaft opposite-side portion 25o.

By increasing the area of the surface of the misload detection inner door 25 and forming the inclined surface having an inclination angle of 1°, the misload of the infusion tube can be detected at a higher accuracy.

Figure 10:
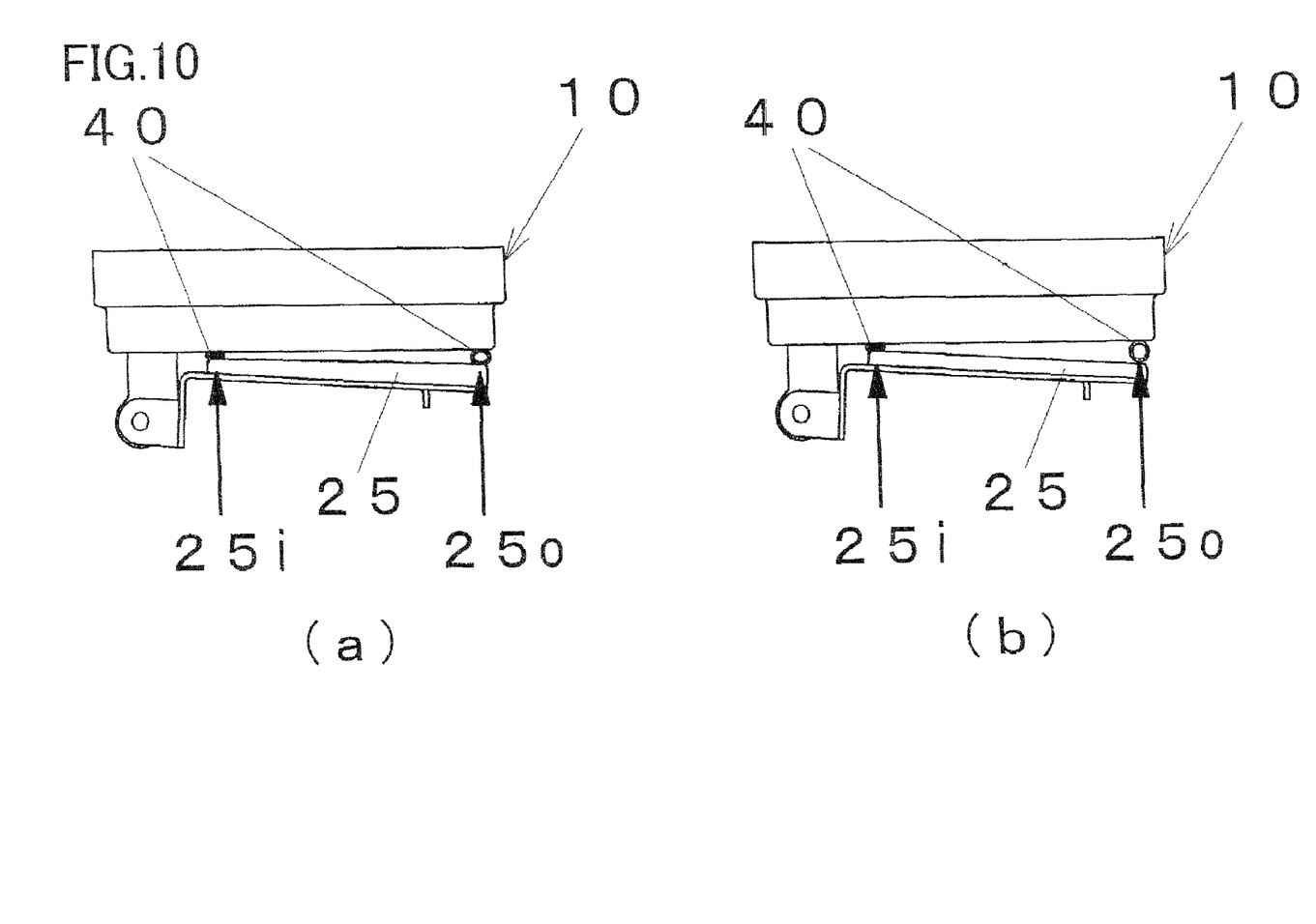
FIG. 10 is a view illustrating a state that the infusion pump according to the embodiment of the present invention is not correctly loaded in the pump body.

The state of detection of misload of the infusion tube according to the embodiment will be described with reference to FIG. 10.

FIG. 10(a) illustrates an example where a surface of a misload detection inner door 25 is formed to have an inclination angle. FIG. 10(b) illustrates anther example where the surface of the misload detection inner door 25 is formed not to have an inclination angle.

In both of the examples of FIGS. 10(a) and (b), opening degrees of a door unit 20 with respect to a pump body 10 are equal to each other. Positional relationships among the misload detection inner door 25, the base plate 11, and the infusion tube 40 at the time of misload of the inner tube are illustrated in the figures.

As shown in FIG. 10(b), in a case where the infusion tube 40 is misloaded in the vicinity of a supporting-shaft side portion, even at the position of the door unit where the misload is detected by contacting the infusion tube 40 with the misload detection inner door 25, if the misload occurs in the vicinity of the supporting-shaft opposite-side portion 25o, the infusion tube 40 is not in contact with the misload detection inner door 25, so that the misload cannot be detected.

Namely, during a series of operations before the door unit 20 is closed with respect to the pump body 10 of the infusion pump 400, the timing of detection of misload of the infusion tube 40 is advancing as the infusion tube approaches the supporting-shaft side portion 25i. The timing is lagging as the infusion tube approaches the supporting-shaft opposite-side portion 25o.

As shown in FIG. 10(a), in case that the surface of the misload detection inner door 25 is formed to have an inclination angle, even if the misleading occurs in the vicinity of the supporting-shaft opposite-side portion 25o, the infusion tube 40 is in contact with the misload detection inner door 25, so that the misload can be detected.

In this manner, by forming a suitable inclination angle on the surface of the misload detection inner door 25, it is possible to improve an accuracy of timing of misload detection for the infusion tube 40 regardless of the misleading position.

In addition, in the embodiment, the inclination angel is set to be 1°. However, the inclination angle may be set to an optimal angle for design according to the relationship among the door supporting shaft, the misload detection inner door of the door unit and the base plate of the pump body or according to applied infusion pumps.

Hereinbefore, embodiments of the infusion pump according to the present invention are described, but various modifications may be implemented without departing from the scope of the present invention.

For example, the feeding mechanism is not limited to the shuttle type, but the tube misload detection mechanism according to the present invention can be applied to any types of infusion pumps that have a door and a handle to feed a solution in an infusion tube in a closed state of the door as well as a peristaltic type.

REFERENCE NUMERALS

10: pump body
11: base plate
11A: latch roller
11c: rectangular through-hole
11d, 11d': groove portion
11s: slide clamp mounting portion
12: shuttle mechanism part
12A: V-grooved driving part
13A: link
13Ai: one end (of link 13A)
14: valve mechanism part
14A: valve
14B: valve
15: slide clamp mechanism part
16: motor
17: lock part
20: door unit
21: door part
22: V-grooved fixing part
23: handle
23A: handle lock part
23Ac: claw portion
23Af: hook portion
24: handle
24c: curved arm portion
25: misload detection inner door
25i: supporting-shaft side portion of misload detection inner door
25o: supporting-shaft opposite-side portion of misload detection inner door
26: stopper mechanism part
26A: stopper
26B: stopper holder
26C: stopper spring
27: door lock part
30: slide clamp
40: infusion tube
100: infusion pump
200: infusion pump
300: infusion pump
400: infusion pump
Y: feeding direction
Y'a: moving direction of claw portion in case of mislead
Y'b: moving direction of stopper in case of mislead
Y'c: moving direction of door lock part in case of misload
Z: moving direction of inner door in case of misload

The invention claimed is:

1. A tubing misload detection mechanism for detecting misloading of an infusion tube in an infusion pump having a pump body, comprising:
    a base plate fixedly disposed on the pump body,
    a first shaft provided on the pump body,
    a door unit hingedly supported by the first shaft, the door unit includes a second shaft,
    a misload-detection inner door hingedly supported by the second shaft, the misload-detection door is sandwiched between the door unit and the base plate when the door unit is in a closed position with the pump body, and
    an interlocking part connected to door unit to engage in a locking position with the base plate when the infusion tube is properly loaded in a predetermined position between the misload-detection inner door and the base plate in the infusion pump,
    wherein the interlocking part is adapted to be unengageable with the base plate, when the infusion tube is improperly loaded and thus pushes directly against the misload-detection inner door and the door unit to prevent a complete closure of the door unit with the pump body.

2. The tubing misload detection mechanism for detecting misloading of an infusion tube in an infusion pump having a pump body according to claim 1,
    wherein the interlocking part includes a claw portion, and
    wherein the base plate includes a latching portion to which the claw portion of the interlocking part latches onto when the infusion tube is properly loaded, and thus allowing a complete closure of the door unit with the pump body.

3. The tubing misload detection mechanism for detecting misloading of an infusion tube in an infusion pump having a pump body as recited in claim 2,
    wherein, when the infusion tube is misloaded and in an improper position between the base plate and the misload-detection door, a gap is created by the infusion tube between the door unit and the base plate and thus preventing the claw portion of the interlocking part from reaching and latching onto the latching portion on the base plate to fully close the door unit.

* * * * *